US007088449B1

(12) United States Patent
Brongersma

(10) Patent No.: US 7,088,449 B1
(45) Date of Patent: Aug. 8, 2006

(54) DIMENSION MEASUREMENT APPROACH FOR METAL-MATERIAL

(75) Inventor: Mark L. Brongersma, Redwood City, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 225 days.

(21) Appl. No.: 10/376,116

(22) Filed: Feb. 28, 2003

Related U.S. Application Data

(60) Provisional application No. 60/425,097, filed on Nov. 8, 2002.

(51) Int. Cl.
*G01N 21/55* (2006.01)
(52) U.S. Cl. ..................................... 356/445; 356/630
(58) Field of Classification Search ................ 356/445, 356/630
See application file for complete search history.

(56) References Cited

U.S. PATENT DOCUMENTS

| 5,028,132 | A | * | 7/1991 | Hickel et al. ............... 356/445 |
| 5,237,392 | A | * | 8/1993 | Hickel et al. ............... 356/445 |
| 5,822,073 | A | * | 10/1998 | Yee et al. .................. 356/445 |
| 5,991,048 | A | * | 11/1999 | Karlson et al. ............. 356/445 |
| 6,373,577 | B1 | * | 4/2002 | Brauer et al. ............... 356/445 |
| 6,395,563 | B1 | | 5/2002 | Eriguchi |
| 6,597,463 | B1 | * | 7/2003 | Singh et al. ................. 356/630 |
| 6,633,392 | B1 | * | 10/2003 | Singh et al. ................. 356/630 |
| 6,704,101 | B1 | * | 3/2004 | Rangarajan et al. ........ 356/630 |
| 6,758,612 | B1 | * | 7/2004 | Tabery et al. ............... 396/569 |
| 6,771,374 | B1 | * | 8/2004 | Rangarajan et al. ........ 356/445 |
| 2001/0040130 | A1 | * | 11/2001 | Lorch et al. ................. 210/601 |
| 2002/0126290 | A1 | * | 9/2002 | Naya ........................... 356/445 |
| 2003/0052084 | A1 | * | 3/2003 | Tabery et al. ................. 216/59 |

OTHER PUBLICATIONS

Hui Wang et al., Method for Electropolishing Metal Film on Substrate, Jul. 22, 2002, U.S. Appl. No. 60/397,941.*

(Continued)

*Primary Examiner*—Layla G. Lauchman
*Assistant Examiner*—Juan Valentin, II
(74) *Attorney, Agent, or Firm*—Crawford Maunu PLLC; Robert J. Crawford

(57) ABSTRACT

Dimensional parameters of metal-containing structures such as films, interconnects, wires and stripes, and nanoparticles are detected using an approach involving plasmon-excitation and one or more metal-constituency characteristics of the metal-containing structures. According to an example embodiment of the present invention, plasmon-exciting light is used to excite plasmons in a structure, the plasmon excitation being responsive to the metal constituency. A characteristic of light reflected from the structure is then used to detect dimensional parameters of the structure. In one implementation, a characteristic of the reflected light that is related to the state of plasmon excitation in the structure is used to detect the dimensional parameters. In another implementation, the angle of incidence of the plasmon-exciting light is used in connection with an intensity-related characteristic of light reflected from structure to detect one or more dimensions of the structure. In still another implementation, the intensity of different wavelengths of the reflected light is used to determine one or more dimensions of the structure. With these approaches, the dimensions of a variety of structures such as metal films, interconnects, wires, and stripes are determined.

35 Claims, 3 Drawing Sheets

OTHER PUBLICATIONS

C. Berger, R. Kooyman, J. Greve, *Surface Plasmon propagation near an index step*, MESA Institute, Applied Optics Group, University of Twente, P.O. Box. 217, 7500 AE Enschede, The Netherlands. Nov. 8, 2002 website printout from http://www.lps.ens.fr/~berger/articles/art4/OptComm.htm, pp. 1-9.

O. Martin, *Breaking the Diffraction Limit with Plasmon Optics: 20 nm Optical Lithography using 600 nm Illumination Wavelength*, Swiss Federal Institute of Technology, IFH, ETZ-G96, Gloriastrasse 35, 8092 Zurich, pp. 1-2.

T. Thio, H.J. Lezec, T.W. Ebbesen, K.M. Pellerin, G.D. Lewen, A. Nahata and R.A. Linke, *Giant Optical Transmission of Sub-wavelength Apertures: Physics and Applications*, TNT2001 Sep. 3-7, 2001, Segovia-Spain, http://www.neci.nj.nec.com/homepages/thio, pp. 1-3.

Diethelm Johannsmann, *Simultaneous Determination of Optical and Acoustic Thickness Using Surface Plasmon Resonance Spectroscopy and Quartz Crystal Microweighing*, Max-Planck-Institute for Polymer Research, Mainz, Germany, pp. 1-16.

*FY 72: Photons and lightwaves, Project 6: Total Internal Reflection and Surface Plasmons*, Nov. 8, 2002 website printout from http://www.fys.sdu.dk/Fys72/html/F72proj6.html, pp. 1-6.

Alec Reader, Philips Analytical, Almelo, The Netherlands, *In-line control of metal & dielectric films*, pp. 1-2.

Rebecca J. Bussjager and H. Angus Macleod, *Using surface plasmon resonances to test the durability of silver-copper films*, Applied Optics, vol. 35, No. 25, Sep. 1, 1996, pp. 1-4.

H. Raether, *Surface Plasmons on Smooth and Rough Surfaces and on Gratings*, Springer, Berlin, 1988, p. 13.

* cited by examiner

DIMENSION MEASUREMENT APPROACH FOR METAL-MATERIAL

RELATED PATENT DOCUMENTS

This patent document is related to Provisional Patent Application Ser. No. 60/425,097, filed on Nov. 8, 2002 (STFD.054P1), to which Applicant claims priority for common subject matter under 35 U.S.C. §120.

FIELD OF THE INVENTION

The present invention relates generally to metal-containing structures, such as metal nanoparticles, metallic nanowires and stripes, and thin metallic films and more particularly to the measurement of structural dimensions of the metal-containing structures and involving devices and approaches therefor.

BACKGROUND

Recent technological advances in the semiconductor industry have permitted dramatic increases in circuit density and complexity, and commensurate decreases in power consumption and package sizes for integrated circuit devices. Single-chip microprocessors now include many millions of transistors operating at speeds of hundreds of millions of instructions per second to be packaged in relatively small, air-cooled semiconductor device packages. A byproduct of these technological advances has been an increased demand for semiconductor-based products, as well as increased demand for these products to be fast, reliable, flexible to manufacture and inexpensive. These and other demands have led to increased pressure to manufacture a large number of semiconductor devices at a rapid pace while increasing the complexity and improving the reliability of the devices.

Integrated circuit fabrication relies heavily on metrology tools that can provide accurate and reliable information related to the dimensions of a variety of structures therein. For example, it is often desirable to obtain the dimensions of active and passive device structures in an integrated circuit, such as interconnects that link electronic transistors and other circuitry in the integrated circuit. Optical techniques that have previously been available for the measurement of structural dimensions typically rely on the interference of light beams reflected from the front and back surface of the structure being measured, and have typically been limited to structures that pass light (e.g., dielectric structures. However, these approaches have not typically been suitable for use with metal structures. Due to the high conductivity of metal structures, the penetration depth of light is usually much less than the metal structure dimensions (i.e., thickness, width or length), with the metal structure often acting like a mirror. In particular, the penetration depth of light in copper varies from about 0.6 nm at the ultraviolet wavelengths ($\lambda$=100 nm) to about 6 nm in the far infrared ($\lambda$=10 $\mu$m). For this reason, a common optical reflection measurement does not yield information relative to certain dimensions of the structure to be measured.

These and other limitations discussed herein have been a challenge in the measurement of structures and in particular to the measurement of various dimensions of structures used in the semiconductor industry.

SUMMARY

The present invention is directed to overcoming the above-mentioned challenges and others related to the types of devices and applications discussed above and in other applications. These and other aspects of the present invention are exemplified in a number of illustrated implementations and applications, some of which are shown in the figures and characterized in the claims section that follows.

Various aspects of the present invention are applicable to obtaining dimensions of a structure having a metal constituency therein. According to one example embodiment of the present invention, dimensions (e.g., thickness, width or length) of the structure are obtained using an optical approach involving a light-induced excitation. Light is directed at the structure and electrons therein are excited, with the electron excitation being dependent upon the metal constituency. A characteristic of the electron excitation is detected and used to obtain dimensions of the structure.

In one particular example embodiment, light-induced collective electron oscillations (i.e., plasmons) are detected and used for determining structural dimensions. In connection with this example embodiment, it has been discovered that the nature of the wavelength of the oscillations is strongly dependent on the optical excitation frequency, the type of metal, and the dimensions of the structure being measured. In this regard, the frequency of the light being directed at the structure and the detected oscillation wavelength are used to determine the dimensions of the structure.

In another example embodiment of the present invention, plasmon-exciting light is directed to a structure having a metal constituency therein, and light reflected from the structure is collected and used for determining one or more dimensions of the structure. The plasmon-excitation affects the reflectivity of the structure and the corresponding intensity of the reflected light can be related to the type of metal and dimensions. In one implementation, the intensity of the collected light is compared to a signature intensity of reflected light for a structure of known composition and geometry, and the comparison is used to determine the dimensions of the structure being analyzed.

In another implementation, plasmon-exciting light is directed toward a structure at a plurality of angles, and the intensity of light reflected from the structure is collected for each of the angles. Angles at which the intensity of reflected light significantly drops (e.g., shows a dip in a plotted curve of intensity versus angle), relative to other angles is used to determine the dimensions of the structure.

Plasmon-exciting light in a variety of wavelengths is directed toward a structure, and the intensity of light reflected from the structure is collected in connection with another example embodiment of the present invention. Wavelengths at which the intensity of reflected light significantly drops (e.g., shows a dip in a plotted curve of intensity versus wavelength), relative to other wavelengths is used to determine the dimensions of the structure.

In another example embodiment of the present invention, a dimension measurement device is adapted for determining structural dimensions using electron oscillations therein. The device includes a light source adapted to direct light toward a structure having a metal constituency. A detection arrangement is adapted for detecting the electron oscillation in response to light from the light source. Using characteristics of the light source, the metal constituency and the detected electron oscillation, the dimensions of the structure are determined. In one particular implementation, the measurement device includes a computer adapted to receive an input related to the detected electron oscillation and further to calculate dimensions of structures having a metallic constituency using the input and a known correlation in connection with the frequency of the light source.

The above summary is not intended to describe each illustrated embodiment or every implementation of the present invention. The figures and detailed description that follow more particularly exemplify these embodiments.

BRIEF DESCRIPTION OF THE DRAWINGS

The invention may be more completely understood in consideration of the detailed description of various embodiments of the invention that follows in connection with the accompanying drawings, in which.

Figure 1:
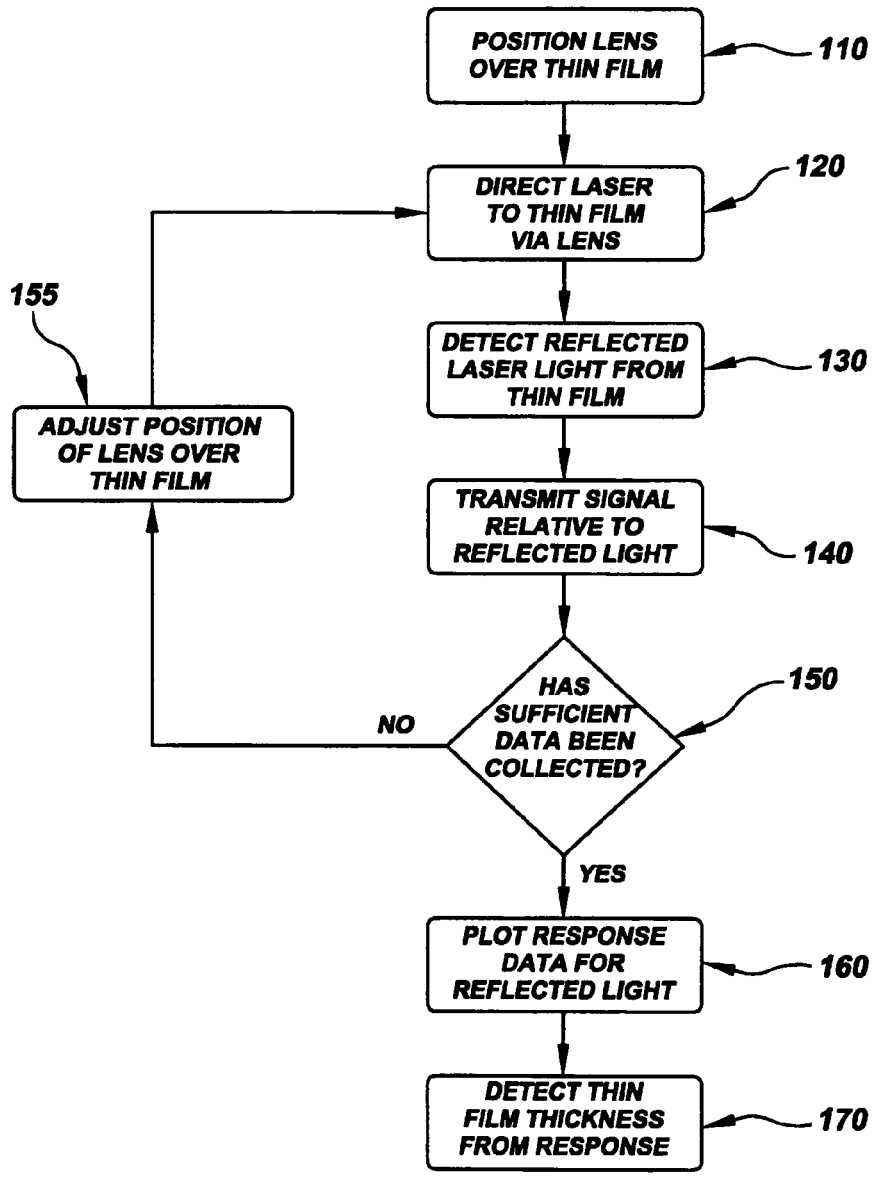
FIG. 1 is a flow diagram for a method of detecting one or more dimensions of metallic structures, according to an example embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be applicable to a variety of different types of devices and processes, and the invention has been found to be particularly suited for semiconductor devices, analysis and manufacture involving approaches to the measurement of a variety of structural dimensions. While the present invention is not necessarily limited to such applications, various aspects of the invention may be appreciated through a discussion of various examples using this context.

According to an example embodiment of the present invention, an optical approach involving light excitation is used for measuring physical dimensions of a structure. Plasmon-exciting light is directed at a structure and electrons therein are excited. A characteristic of reflected light related to the electron excitation is used to identify a dimensional parameter of the structure.

According to a more particular example embodiment of the present invention, a non-invasive optical approach is used to detect a dimensional characteristic of a structure having a metal constituency including one or more metals such as copper, gold, aluminum and silver. In various implementations, the structures for which dimensions are being obtained are circuit components of an integrated circuit device, for example, having a typical dimensions of between about a few microns and a few hundred nanometers. Light is directed toward the metal-containing structure and interacts with the metal to excite surface plasmons therein. As discussed above, the surface plasmon wavelength is strongly dependent on both the optical excitation frequency and the dimensions of the structure. A reflection of the light has characteristics that are dependent upon the plasmon wavelength. The dependency of the reflected light characteristics upon structural dimensions (and plasmon wavelength) is utilized to obtain fast, accurate and non-invasive measurement of the dimensions of the metal-containing structure.

In one particular implementation, empirical tests (e.g., computer simulations) are carried out on structures having known dimensions to identify a correlation between plasmon wavelength, light source frequency, and the dimensions for a structure having a particular metal constituency therein. This correlation is used during subsequent analysis to determine the dimensions of the structure when the light source frequency is known and wherein the plasmon wavelength is detected. With this approach, dimensions of a variety of different structures are detected using a relatively fast and easy correlation approach.

FIG. 1 is a flow diagram for detecting the dimensions of a structure according to another example embodiment of the present invention. At block 110, a lens is positioned over a structure, and laser light is directed through the lens toward a structure having a metal constituency therein at block 120. The laser light reaches the structure and reflects therefrom, with characteristics of the reflection being responsive to the dimensions of the structure and the metal constituency therein. The reflected light is then detected at block 130 and used to create a signal indicative of the intensity of the reflected light, with the signal being transmitted at block 140 for data collection (e.g., using a computer). The process is repeated with the lens being re-adjusted at block 155, the laser light again being directed to the structure via the re-positioned lens, with a corresponding intensity signal being transmitted. The repetition is continued until sufficient data has been collected to show a significant change in intensity of the detected light (i.e., as a function of the reflection angle) at a particular lens position, as shown in block 150. Once sufficient data is available, response data is plotted for the reflected light at block 160 (e.g., as shown on display 242 of FIG. 2, discussed below). Using the response data, a significant change in intensity at a particular lens position is noted and correlated to a particular dimension of the structure that relates to the change in intensity at block 170 for detecting the dimension.

Figure 2:
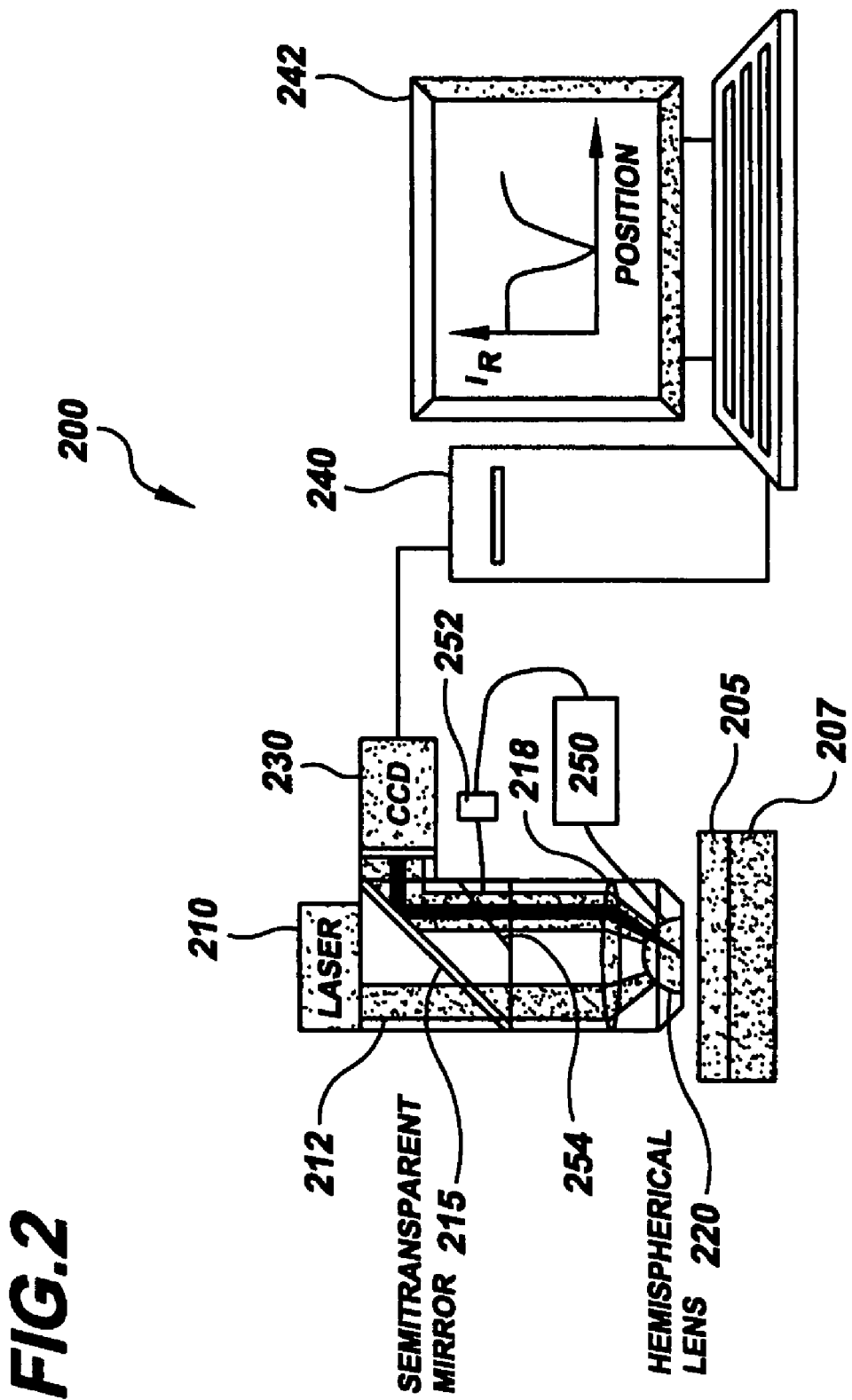
FIG. 2 shows structural dimension detection and an arrangement therefor, according to another example embodiment of the present invention.

FIG. 2 shows a dimensional detection arrangement 200 and approach for determining the dimensions of a metal-containing structure 205 on an insulating substrate 207 using an optical reflection measurement approach, according to an example embodiment of the present invention. A monochromatic laser beam 212 from a laser 210 (e.g., with a power of about 100 mW) is passed through a semitransparent mirror 215 and focused on the back surface of a hemispherical lens 220 using a focusing lens 218. The angle of incidence of the laser beam to the hemispherical lens 220 is chosen such that the beam undergoes total internal reflection and sets up an evanescent wave at the back surface of the hemispherical lens 220. The hemispherical lens 220 is brought into the proximity of the copper structure and the evanescent light wave therefrom is strongly coupled to conduction electrons in the metal-containing (e.g., copper) structure 205 to create plasmon waves therein.

A reflected light beam from the metal-containing structure 205 passes through the hemispherical lens 220, the focusing lens 218 and the semitransparent mirror 215 and is then collected at a CCD cameral 230. The CCD camera 230 is coupled to a computer 240 with a display 242 and adapted to interpret data from the CCD camera and to display the intensity of the collected light versus position (relative to the angle of incident light upon the metal-containing structure 205). In one implementation, a set of incidence angles is simultaneously investigated, with the angle-dependent optical reflectivity of the metal-containing structure being visualized with the CCD camera.

In connection with this approach, the dimensions of the metal-containing structure 205 are determined from the reflected intensity map on the display 242 (e.g., using software that is based on electromagnetic theory. The excitation efficiency of plasmons in a metal structure is strongly dependent on the incidence angle of the light upon the metal-containing 205, as controlled in the dimensional detection arrangement 200. At a certain incidence angle or range of incidence angles, a large fraction of the incident electromagnetic energy from the laser beam passing to the metal-containing structure 205 is converted to kinetic energy of the electrons (e.g., a plasmon wave is excited). As a result, the intensity of the reflected beam is significantly reduced. At other angles of incidence the corresponding specularly reflected laser beam has a much higher intensity because no energy is converted (lost) to plasmon waves generated in the metal-containing structure 205. The angle-dependent reflectivity is imaged using the CCD to produce an image on the display 242.

In a more particular implementation, the dimensional detection arrangement 200 includes a positioning arrangement 250 adapted to position the hemispherical lens 220. The positioning arrangement includes motors and other mechanical apparatus (e.g., gears, linkages) coupled to the hemispherical lens 220 for positioning. The positioning is optionally effected using a portion of the light reflected from the metal-containing structure 205 using a beam splitter 254 and a light detector 252. A signal from the light detector 252 is coupled to the positioning arrangement 250. In one implementation, the positioning arrangement 250 is adapted to position the hemispherical lens 220 very close (e.g., a few hundred nanometers) to the metal-containing 205. In another implementation, the positioning is effected using the signal from the reflected light such that a slight drop in the signal is indicative of the evanescent wave "hitting" the metal-containing structure 205.

The metal-containing structure 205 is accessed to determine a dimension using one or more approaches, depending upon the application and available equipment. In one implementation, the metal-containing 205 is near the edge of an integrated circuit chip, for instance, where a semiconductor wafer is cut. In another implementation, the metal-containing structure 205 is part of a test structure on an integrated circuit chip where copper has been deposited directly onto the underlying layer 207 (e.g., Si or $SiO_2$). Moreover, in various other implementations, the dimensional detection arrangement 200 is adapted for detecting the structural dimensions on a different type of integrated circuit device than that shown, for instance, without necessarily having a metal-containing structure over an insulating substrate 207.

In another example embodiment of the present invention, dimensions of a metal-containing structure are measured using far-field excitation to excite plasmons in metallic nanoparticles in the metal-containing structure. For instance, the nanoparticles may be patterned structures on a surface of a film, or may be part of a roughness characteristic of a film. In connection with this example embodiment, it has been discovered that the wavelength of the far-field excitation for sufficient excitation (e.g., enough excitation to detect a response for the detection of structural dimensions) depends upon the size, shape, and periodicity of the structures. For example, the reflection spectrum (intensity vs. wavelength or intensity vs. reflection angle) of a periodic array of nanoparticles on the surface of a metal film show a sharp minimum at such a sufficient excitation. At this wavelength, electromagnetic energy is efficiently taken out off the incident beam and is converted to plasmon motion. With this approach, the shape dependence of the wavelength can be used in connection with detected intensity at a particular wavelength to detect the dimensional characteristics of the metal structure.

Variations in dimensions across a structure are detected in connection with another example embodiment of the present invention. For instance, by applying one or more of the approaches discussed in connection with FIG. 2 at different locations on a structure, the dimensions at these various locations are detected. In one particular implementation, the detected dimensions are mapped to a location and used to generate a contour map of the structure.

According to another example embodiment, and again referring to FIG. 2, a plot as shown on display 242 is obtained for a plurality of materials having known dimensions. Signatures (plots for a particular material with known dimensions) are thus established for materials having a known constituency and corresponding dimension thereof. Using these signatures, a plot is obtained for a structure having an unknown dimension and/or material type. This obtained plot is compared to signature plots and, therefrom, the material and/or dimension of the sample are identified when plots match (or nearly match). In one implementation, the signatures are obtained using an actual measurement of a structure having known material/dimensions therein. In another implementation, electromagnetic simulations are used to predict the signature for a particular metal with dimensions therefrom. For more information regarding such prediction, reference may be made to the attached appendices in connection with Maxwell's equations (see, e.g., page 2 of "Photons and lightwaves"), attached hereto in an appendix.

Figure 3:
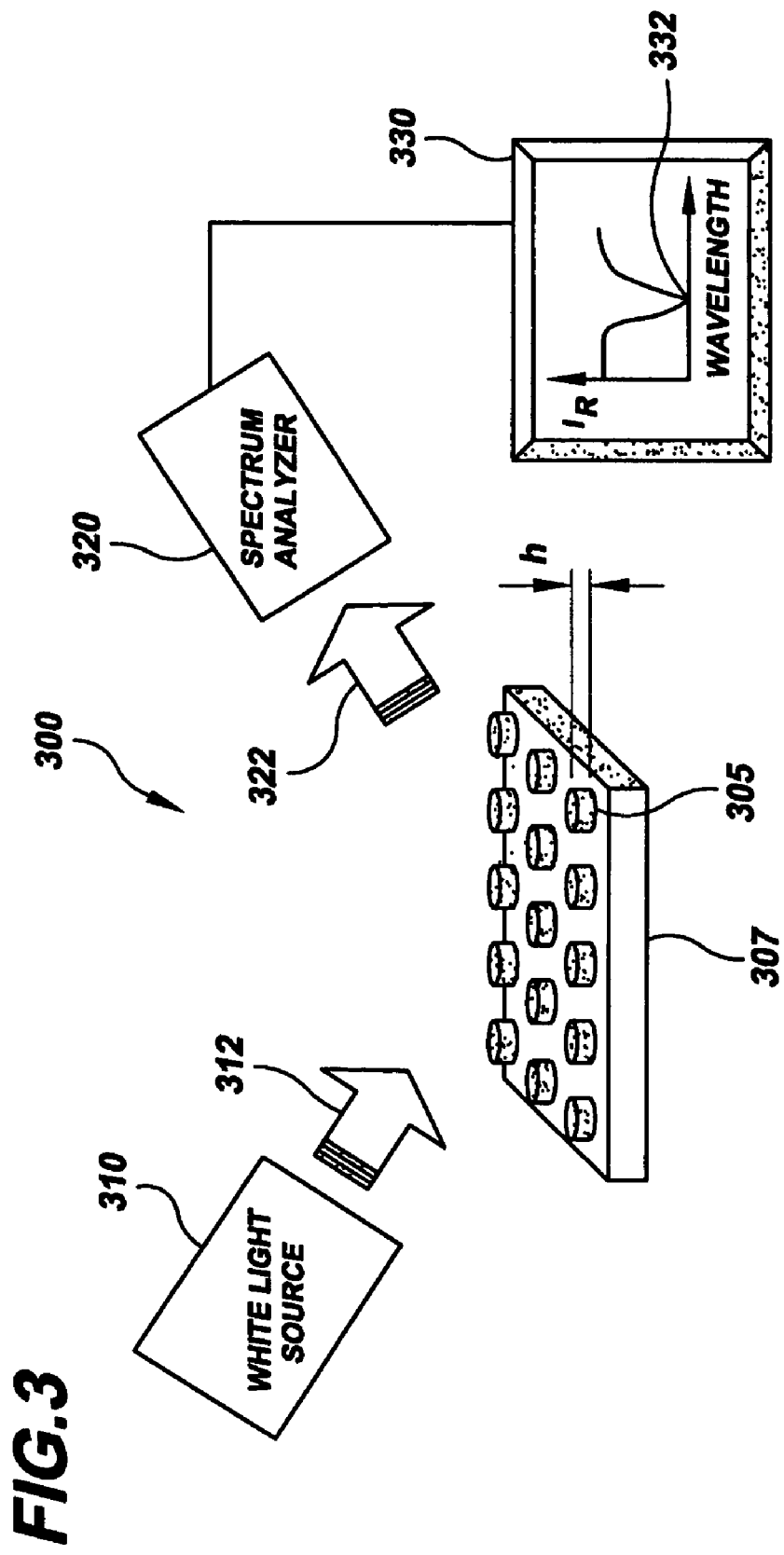
FIG. 3 shows another approach to dimension detection and an arrangement therefor, according to another example embodiment of the present invention.

FIG. 3 shows one particular approach to far-field excitation using a dimensional detection system 300, according to another example embodiment of the present invention. The system 300 includes a white light (far-field) source 310 adapted to direct light 312 towards a plurality of patterned structures, including nanoparticle 305, on a surface 307 (e.g., an insulating layer). Light 322 reflected from the patterned structure is detected by a spectrum analyzer 320 adapted to detect intensity of the reflected light. Intensity versus wavelength is optionally plotted on a display 330, and is further used to identify a dimensional characteristic of the nanoparticles. The intensity drop indicated by node 322 on the display 330, depends strongly on the height, h, of the nanoparticles from which the light 322 is reflected. For more information regarding the correlation of height versus intensity of the reflected light at different wavelengths, which may be used in connection with this example embodiment, reference may be made to the attached appendices in connection with Maxwell's equations (see, e.g., page 2 of "Photons and lightwaves." With this approach, the resulting measurement is not necessarily dependent upon the angle of the incident light 312.

In one implementation, one or more dimensions of particles with a well-defined cross-section (e.g., with a diameter less than the excitation wavelength) patterned on a specified test-area on a silicon wafer are measured. Referring to FIG. 3 and using this approach, each of the nanoparticles, including nanoparticle 305, are patterned on a silicon wafer (307), each having similar cross-sections and height h. The light 312 is then directed at the patterned nanoparticles, with the dimensions thereof being detected via reflected light 322, as discussed above.

In another example embodiment of the present invention, foreign material (e.g., corrosion or oxidation) on a surface is detected using one or more of the approaches discussed herein. For example, when small spots of corrosion are present on circuitry, an approach not inconsistent with that discussed in connection with FIG. 3 is used to identify the presence thereof, as well as dimension (e.g., thickness and/or width) of the corrosion. In another example, when oxidation exists on circuitry, an approach not inconsistent with that discussed in connection with FIG. 2 is used to detect the presence and dimensions of the oxidation.

In one particular implementation, the foreign material discussed above is detected using a comparison between an expected reflection from the surface and the reflection detected from the corrosion itself. For instance, when a metal such as copper oxidizes, copper oxide is formed on a surface thereof. Using one or more of the approaches discussed herein, a reflection is obtained from the copper oxide and used to plot response characteristics of the reflection. By analyzing the response characteristics of the reflection (which depend, e.g., upon the refractive index of the material from whence the reflection came), it is determined whether the response is characteristic of the surface itself (copper) or the oxide (copper oxide). In one particular approach, subtle differences in reflection characteristics are identified as being responsive to a corroded surface, such that a range of responses can be used to detect dimensions of the structure and the thickness of a corrosion layer thereon. With this approach, and without necessarily detecting the dimensions of the corrosion layer, corrosion such as oxidation and others existing on a surface are readily detected.

A semiconductor chip is analyzed after manufacturing using an approach involving one or more of the approaches to dimension detection as discussed herein, according to another example embodiment of the present invention. A circuit element (e.g., an interconnect) of the chip is accessed, for example, either via an exposed portion or by removing material in the chip to expose the circuit element. Laser light is directed to the exposed circuit element to excite plasmons therein. Reflections from the laser light, which are affected by the plasmon excitation, are used to detect the dimensions of the circuit element. In one particular implementation, the circuit element is analyzed to detect whether it has a specified design dimension (or, for instance, is within an acceptable range of dimensions. A dimensional defect is identified as reflections that indicate that one or more dimensions of the circuit element are different from the specified design dimensions.

Electromigration in metal structures is detected using an approach involving one or more of the plasmon excitation approaches discussed herein, according to another example embodiment of the present invention. A laser is spot-scanned across a metal structure such that dimensional variation across the structure is detected (e.g., using an approach as discussed in connection with FIG. 2, dimensional characteristics at a plurality of locations on the structure are detected). Portions of the structure that are smaller than other portions of the structure are identified as exhibiting electromigration.

For background information that may be used in understanding the above-description, as well as attributes, implementations and other applications thereof, and for specific information regarding approaches that may be used in connection with one or more example embodiments of the present invention, reference may be made to the following articles as well as any additional publications incorporated therein, attached hereto in an Appendix:

[1] C. Berger, R. Kooyman, J. Greve. *Surface Plasmon propagation near an index step*. MESA Institute, Enschede, 9 pgs. (website printout Nov. 8, 2002).

[2] O. Martin. *Breaking the Diffraction Limit with Plasmon Optics: 20 nm Optical Lithography using 600 nm Illumination Wavelength*. Swiss Federal Institute of Technology, Zurich, 2 pgs.

[3] T. Thio, H. J. Lezec, T. W. Ebbesen, K. M. Pellerin, G. D. Lewen, A. Nahata, R. A. Linke. *Giant Optical Transmission of Sub-Wavelength Apertures: Physics and Applications*. TNT2001 Website, Segovia, 3 pgs. (printout dated Sep. 3–7, 2001).

[4] D. Johannsmann. *Simultaneous Determination of Optical and Acoustic Thickness Using Surface Plasmon Resonance Spectroscopy and Quartz Crystal Microweighing*. Max-Planck-Institute for Polymer Research, Mainz, 16 pgs.

[5] FY 72:P *Photons and lightwaves*. (Website: www.fys.s-du.dk, 6 pgs. Printout Nov. 8, 2002).

While the present invention has been described with reference to several particular example embodiments, those skilled in the art will recognize that many changes may be made thereto. For instance, various ones of the dimensional measurement scenarios discussed herein may be implemented using a variety of approaches; the wavelength-dependent approaches and the incident-angle dependent approaches may be interchanged. For instance, the wavelength approach discussed in connection with FIG. 3 may be implemented with a thin film or other structure, rather than small patterned nanoparticles. Similarly, the angle-dependent approach discussed in connection with FIG. 2 may be implemented with nanoparticles, as shown in FIG. 3. These and other changes may be made without departing from the spirit and scope of the present invention.

What is claimed is:

1. A method for obtaining a dimensional parameter of a structure having a metal constituency and a corresponding plasmon-based metal constituency characteristic, the method comprising:

directing light including plasmon-exciting light toward the structure;

collecting light reflected from the structure, said structure having a metal constituency; and obtaining a dimensional parameter of the structure as a function of the collected light and the plasmon-based metal constituency characteristic.

2. The method of claim 1, further comprising:

providing a plurality of known signature light reflection characteristics for a plurality of dimensions of the structure based on the plasmon-based metal constituency; and wherein obtaining a dimensional parameter of the structure as a function of the collected light and the plasmon-based metal constituency characteristic includes comparing the collected light to the plurality of known signature light reflection characteristics and obtaining therefrom a match.

3. The method of claim 1, wherein obtaining a dimensional parameter of the structure as a function of the collected light and the plasmon-based metal constituency characteristic includes detecting a reflectivity characteristic of the structure and obtaining the dimensional parameter from the detected reflectivity characteristic and the plasmon-based metal constituency characteristic.

4. The method of claim 3, wherein obtaining the dimensional parameter from the detected reflectivity characteristic includes obtaining the dimensional parameter as a function of the intensity of the directed light that is reflected and the plasmon-based metal constituency characteristic.

5. The method of claim 4, wherein directing light including plasmon-exciting light includes directing monochromatic light at a plurality of angles to the structure, wherein detecting a reflectivity characteristic of the structure includes detecting the intensity of the collected light using different ones of the plurality of angles and wherein obtaining the dimensional parameter includes comparing the intensity at different ones of the plurality of angles.

6. The method of claim 4, wherein directing light including plasmon-exciting light includes directing white light and wherein detecting a change in a reflectivity characteristic includes detecting a particular wavelength of the collected light having an intensity that is significantly less than the intensity of other wavelengths of the collected light.

7. The method of claim 1, wherein directing light including plasmon-exciting light toward the structure includes exciting plasmons in the structure as a function of the angle of light incident upon the structure and wherein obtaining a dimensional parameter of the structure includes identifying the angle of light incident upon the structure that causes a selected condition of plasmon excitation in the structure.

8. The method of claim 7, further comprising directing light toward the structure using at least two incident angles and wherein identifying the angle of light incident upon the structure that causes a selected condition of plasmon excitation in the structure includes identifying one of the two incident angles as causing a drop in intensity of the reflected light, relative to the intensity of the reflected light using another one of the at least two incident angles.

9. The method of claim 1, wherein collecting light reflected from the structure includes detecting the intensity of the reflected light at a plurality of wavelengths and wherein obtaining a dimensional parameter of the structure as a function of the collected light and the plasmon-based metal constituency characteristic includes detecting a wavelength at which the collected light exhibits a drop in intensity, relative to other wavelengths and using the detected wavelength exhibiting the drop in intensity to detect the dimension of the structure from which the collected light is reflected.

10. The method of claim 1, wherein obtaining a dimensional parameter of the structure includes identifying the dimensions of a metal circuit in a semiconductor device for post-manufacturing defect analysis of the semiconductor device.

11. The method of claim 1, wherein obtaining dimensional parameter of the structure includes obtaining a dimensional parameter of contaminants on a surface.

12. The method of claim 1, wherein directing light including plasmon-exciting light toward the structure includes spot-scanning a laser across the structure and wherein obtaining a dimensional parameter of the structure as a function of the collected light and the plasmon-based metal constituency characteristic includes detecting a variation in dimensions of the structure.

13. The method of claim 12, wherein detecting a variation in dimensions of the structure includes detecting a variation in the dimensions of the structure that is due to electromigration.

14. The method of claim 1, wherein collecting light reflected from the structure includes detecting a refractive index from the structure, further comprising:

detecting a composition parameter of the structure in response to the refractive index.

15. The method of claim 14, wherein detecting a composition parameter of the structure in response to the refractive index includes detecting a variation in composition from a signature composition and, therefrom, identifying the variation in composition as a contaminant on the surface of the structure.

16. A method for measuring a dimensional parameter of a structure having a certain metal constituency, the method comprising:

directing light including plasmon-exciting light toward the structure, said structure having a metal constituency;

in response to the light reflecting from the structure, collecting angle-dependent reflectivity information; and using the angle-dependent reflectivity information to determine a dimensional parameter of the structure.

17. The method of claim 16, wherein directing light includes directing light toward the structure at a plurality of angles of incidence, wherein collecting angle-dependent reflectivity information includes detecting the intensity of the reflected light at selected ones of the plurality of angles of incidence and wherein using the angle-dependent reflectivity information to determine a dimensional parameter of the structure includes detecting an incident angle at which the intensity of the reflected light significantly drops, relative to other ones of the plurality of incident angles.

18. The method of claim 17, wherein using the angle-dependent reflectivity information to determine a dimensional parameter of the structure includes comparing the incident angle at which the intensity of the reflected light drops to a signature angle and, therefrom determining the dimensional parameter.

19. The method of claim 18, wherein comparing the incident angle at which the intensity of the reflected light drops to a signature angle includes plotting the incident angle versus intensity of the reflected light and comparing the plot to at least one signature plot and determining the dimensional parameter in response to the comparison of the plots.

20. The method of claim 17, wherein using the angle-dependent reflectivity information to determine a dimensional parameter of the structure includes comparing using the incident angle at which the intensity of the reflected light drops in a mathematical formula to determine the dimensional parameter.

21. A method for measuring a dimensional parameter of a structure having patterned material on a surface thereof, the patterned material having a certain metal constituency, the method comprising:

directing light including plasmon-exciting light toward the patterned material, said patterned material having a metal constituency;

in response to the light reflecting from the patterned material, collecting wavelength-dependent reflectivity information; and using the wavelength-dependent reflectivity information to detect a dimensional parameter of the patterned material.

22. The method of claim 21, wherein collecting wavelength-dependent reflectivity information includes collecting intensity information at a plurality of wavelengths of the reflected light and wherein using the wavelength-dependent reflectivity information to detect a dimensional parameter of the patterned material includes identifying a wavelength of light in the reflected light that exhibits a significant drop in intensity, relative to other wavelengths in the reflected light.

23. The method of claim 21, wherein using the wavelength-dependent reflectivity information to detect a dimensional parameter of the patterned material includes comparing the wavelength that exhibits the significant drop in intensity to a signature reference and identifying a dimensional parameter of the patterned material that corresponds to the wavelength exhibiting the significant drop in intensity.

24. The method of claim 23, wherein comparing the wavelength that exhibits the significant drop in intensity to a signature reference includes plotting the wavelength versus intensity of the reflected light and comparing the plot to a plot of wavelength versus intensity for a plurality of structures having known dimensions and determining the dimensional parameter in response to the comparison.

25. A system for measuring a dimensional parameter of a structure having a metal constituency and a corresponding plasmon-based metal constituency characteristic, the system comprising:
light-sourcing means for directing light including plasmon-exciting light toward the structure, said structure having a metal constituency;
means for collecting light reflected from the structure; and
means for obtaining a dimensional parameter of the structure as a function of the collected light and the plasmon-based metal constituency characteristic.

26. A system for measuring a dimensional parameter of a structure having a metal constituency and a corresponding plasmon-based metal constituency characteristic, the system comprising:
a light source adapted to direct light including plasmon-exciting light toward the structure, said structure having a metal constituency;
an optical receiving device adapted to collect light reflected from the structure; and
a processing circuit programmed to obtain a dimensional parameter of the structure as a function of the collected light and the plasmon-based metal constituency characteristic.

27. A method for obtaining a dimensional parameter of a structure having a metal constituency and a corresponding plasmon-based metal constituency characteristic, the method comprising:
directing light including plasmon-exciting light toward the structure, said structure having a metal constituency;
collecting light reflected from the structure; and
obtaining a depth measurement of the structure as a function of the collected light and the plasmon-based metal constituency characteristic.

28. The method of claim 27, further comprising:
providing a plurality of known signature light reflection characteristics for a plurality of dimensions of the structure based on the plasmon-based metal constituency; and
wherein obtaining a depth measurement of the structure as a function of the collected light and the plasmon-based metal constituency characteristic includes comparing the collected light to the plurality of known signature light reflection characteristics and obtaining therefrom a match.

29. The method of claim 27, wherein obtaining a depth measurement of the structure as a function of the collected light and the plasmon-based metal constituency characteristic includes detecting a reflectivity characteristic of the structure and obtaining the depth measurement from the detected reflectivity characteristic and the plasmon-based metal constituency characteristic.

30. The method of claim 29, wherein obtaining the depth measurement from the detected reflectivity characteristic includes obtaining the depth measurement as a function of the intensity of the directed light that is reflected and the plasmon-based metal constituency characteristic.

31. The method of claim 30, wherein directing light including plasmon-exciting light includes directing monochromatic light at a plurality of angles to the structure, wherein detecting a reflectivity characteristic of the structure includes detecting the intensity of the collected light using different ones of the plurality of angles and wherein obtaining the depth measurement includes comparing the intensity at different ones of the plurality of angles.

32. The method of claim 30, wherein directing light including plasmon-exciting light includes directing white light and wherein detecting a change in a reflectivity characteristic includes detecting a particular wavelength of the collected light having an intensity that is significantly less than the intensity of other wavelengths of the collected light.

33. The method of claim 27, wherein directing light including plasmon-exciting light toward the structure includes exciting plasmons in the structure as a function of the angle of light incident upon the structure and wherein obtaining a depth measurement of the structure includes identifying the angle of light incident upon the structure that causes a selected condition of plasmon excitation in the structure.

34. The method of claim 27, wherein the structure includes a circuit and wherein obtaining the depth measurement of the structure includes identifying a depth dimension of a film on the circuit.

35. The method of claim 27, wherein obtaining the depth measurement of the structure includes obtaining a depth measurement of a contaminant on a film.

* * * * *